United States Patent [19]

Chapman

[11] 4,073,288
[45] Feb. 14, 1978

[54] BLOOD SAMPLING SYRINGE

[76] Inventor: Samuel L. Chapman, 2814 Conner St., Port Huron, Mich. 48060

[21] Appl. No.: 698,270

[22] Filed: June 21, 1976

[51] Int. Cl.² ............................................. A61B 5/14
[52] U.S. Cl. .............................. 128/2 F; 128/DIG. 5
[58] Field of Search ................ 128/2 F, DIG. 5, 216, 128/218 C, 218 P, 218 PA, 218 R

[56] References Cited

U.S. PATENT DOCUMENTS

| 2,102,785 | 12/1937 | Brooks | 128/DIG. 5 X |
|---|---|---|---|
| 2,250,467 | 7/1941 | Cole | 128/218 C |
| 2,594,621 | 4/1952 | Derrick | 128/DIG. 5 X |
| 2,744,527 | 5/1956 | Barrett et al. | 128/216 |
| 2,832,344 | 4/1958 | Davidson | 128/DIG. 5 X |
| 3,143,109 | 8/1964 | Gewertz | 128/DIG. 5 X |
| 3,161,194 | 12/1964 | Chapman | 128/218 R |

Primary Examiner—Kyle L. Howell
Attorney, Agent, or Firm—A. Mercedes

[57] ABSTRACT

This blood sampling syringe consists primarily of a cylinder, which removably receives an expandable encasement, that will receive a specimen by needle means. The upper structure of this syringe includes rotatable cylinder means for creating a vacuum, which will be controlled by an adjustable control valve. The control valve enables the user to utilize as much of the vacuum needed to collect a specimen within the disposable and expandable encasement.

3 Claims, 2 Drawing Figures

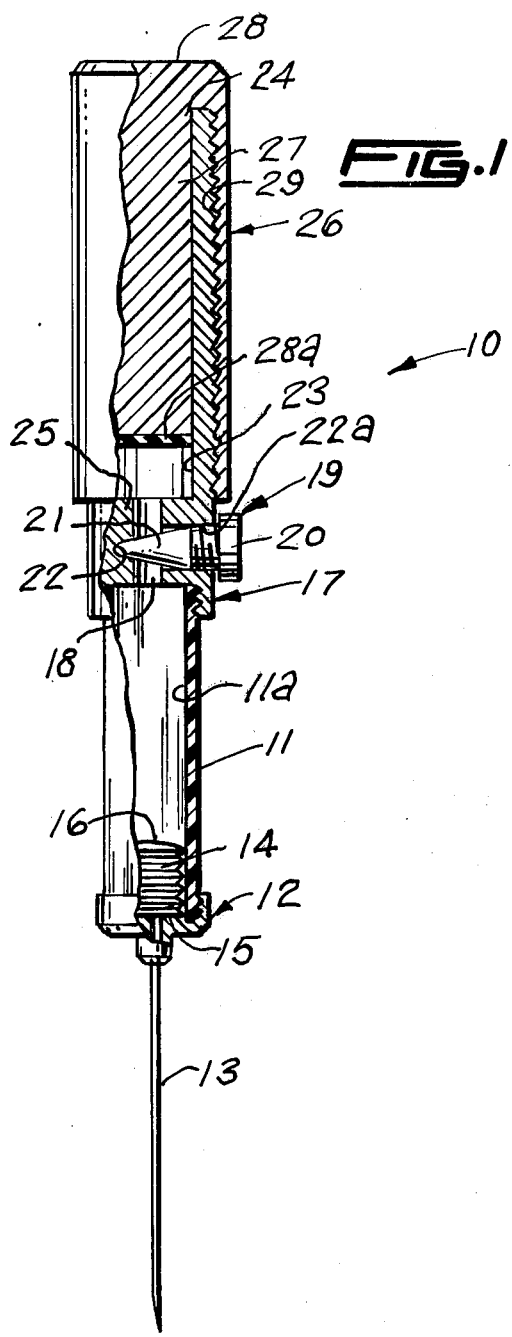
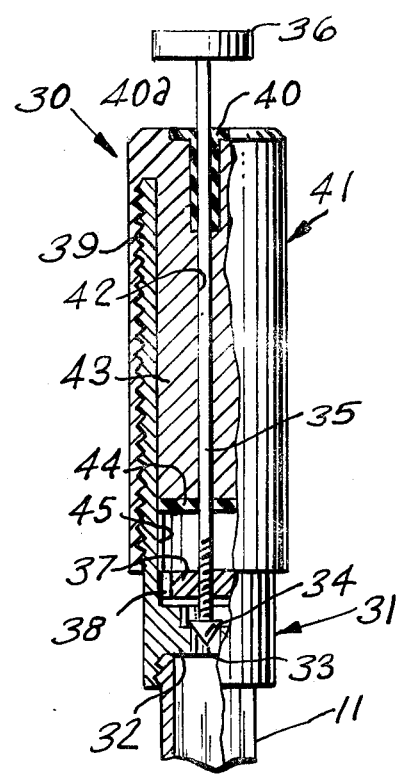

BLOOD SAMPLING SYRINGE

This invention relates to hypodermic syringes, and more particularly, to a vacuum type hypodermic syringe.

It is, therefore, the principal object of this invention to provide a hypodermic syringe, which will be used to extract specimens under controlled conditions.

Another object of this invention is to provide a syringe of the type described, which will produce a vacuum to extract specimens, while, simultaneously, greatly reducing the chance of accidentally injecting air into the circulatory system.

A further object of this invention is to provide a syringe, of the type described, which will employ the use of an expandable encasement, which is disposable, as according to the teachings of Samuel L. Chapman, U.S. Pat. no. 3,161,194.

A still further object of this invention is to provide a syringe of the type described, which will employ the use of rotary motion to produce a vacuum.

Other objects of the invention are to provide a blood sampling syringe, which is simple in design, inexpensive to manufacture, economical to operate, rugged in construction, easy to use and efficient in operation.

These and other objects will be readily evident upon a study of the following specification, and the accompanying drawing, wherein:

FIG. 1 is a vertical view of the present invention, shown in elevation and partly broken away;

FIG. 2 is a fragmentary view, in elevation, of a modified form of the invention, which shows a second form of valve for controlling the vacuum produced on the specimen receiving and disposable encasement.

According to this invention, a blood sampling syringe 10 is shown to include a classic cylinder 11, which is externally threaded, one end threadably receiving a cap, 12 having a hollow needle 13 therein. A plastic encasement 14, of accordian-like configuration, is expandable by vacuum means, within the cylinder bore 11a. Encasement 14 is fixedly secured by its end wall 15, in a suitable manner, within cap 12, and the end wall 16 is freely and slideably received within the bore 11a of cylinder 11, when vacuum is produced within bore 11a.

A cylindrical control valve body 17 is threadably received on the opposite end of cylinder 11, and an opening 18 within valve body 17 enables air to be withdrawn from cylinder 11. A valve screw 19, having a head 20, is of a suitable plastic material, for a purpose which hereinafter will be described. Valve screw 19 is provided with a conical end 21, which is removably received within recess 22, the conical end 21 serving as a means of restricting opening 18. Valve screw 19 is threadably received within opening 22a, which intersects opening 18, and valve screw 19 is of plastic material, so as to provide sealing means against air entering cylinder bore 11a. Bore 23 of body 17 is in longitudinal alignment with opening 18 and the bore 11a of cylinder 11. Control valve body 17 includes an open end 24, and the recessed end wall 25, which abuts with cylinder 11, is a control valve assembly. An internally threaded cylinder 26 threadingly engages the externally threaded upper portion of body 17, and cylinder 26 is provided with a shank portion 27, which is integral with and extending from end wall 28. A rubber or plastic disc 28a provides seal means, in a manner which hereinafter will be described. The annular opening 29 enables cylinder 26 to be threaded downwards to the control valve assembly, and enables shank 27 to rotatably engage with the bore 23. Disc 28a is fixedly secured to the end of shank 27 in a suitable manner, and is in rotatable engagement with bore 23, so as to prevent air from entering bore 23, past the threaded portion of cylinder 26 and control valve body 17.

In use, cylinder 26 is first rotated downwards upon the control valve body 17, to its stopping point, after valve screw 19 is rotated outwards of control body 17, so as to have air at atmosphere pressure within syringe 10. Valve screw 19 is then rotated until it seals off opening 18. Cylinder 26 is then rotated upwards on control valve body 17, which by means of shank 27 and disc 28a will cause a vacuum to be created in bore 23. The valve screw 19 can then be rotated outwards, so as to release this energy source, at will, to cause the collapsible encasement 14, to fill with the specimen obtained through the needle 13 means.

As shown in FIG. 2 of the drawing, a modified form of valve assembly 30 is shown to include a cylinder 31, having a recessed end wall 32, through which is an opening 33. A conically configurated valve 34 is seatable over opening 33, and valve 34 has, secured on its stem 35, a control knob 36, for the rotation thereof. A disc 37 is fixedly secured, in a suitable manner, within cylinder 31, and is spaced apart from the recessed end wall 32. An offset passage opening 38 through disc 37 provides for vacuum passageway means through cylinder 11. The upper portion 39 is similar to valve body 17, of the heretofore described embodiment of the present invention, with the exception, that a rubber or plastic seal 40 is secured within the end wall 40a of cylinder 41, so as to provide shield means for stem 35, which is rotatably received within the opening 42 of the shank 43, which has secured fixedly thereto, a rubber or plastic disc 44 which serves as seal means for the shank 43 and the cylinder 31.

The means for creating a vacuum with valve assembly 30, is similar to that described of FIG. 1 of the drawing, with the exception, that control knob 36, through the valve 34 means, may control the vacuum as desired through the opening 33, the passage 38, and the bore 45.

What I claim is:

1. A blood sampling syringe, comprising a hollow cylinder which is closed off by hollow needle means at one end, for receiving a specimen, an expandable encasement means sealingly positioned around the opening of said needle into said cylinder, said encasement means serving to receive said specimen, a cylindrical control valve body threadingly received on the opposite end of said cylinder, by the end wall means of said control valve body, a passage extending through said control valve body, a screw valve means operating transversely of said passage in said control valve body for opening and closing said passage, a bore in said control valve body and communicating with said passage at an end opposite from said hollow cylinder such that said screw valve means is located between said hollow cylinder and said bore, a solid and cylindrical shank means sealingly and slidably positioned in said bore to provide means for creating a vacuum in said bore when said screw valve means is positioned to close said passage and to subsequently draw a specimen through said needle when said screw valve means is positioned to open said passage.

2. The combination according to claim 1, wherein said shank means has fixedly secured to its end, a flexible disc forming seal means within the said bore of said control valve body, said flexible disc being in sliding abutment on its outer periphery with the inner periphery of said bore of said control valve body.

3. The combination according to claim 2, wherein said screw valve means is of flexible plastic material, so as to provide sealing means on its outer periphery, with the opening of said control valve body which receives said screw valve means, the shank of said screw valve means being conical in cross-sectional configuration at one end, said conical end of said screw valve means being removably received within said passage of said control valve body.

* * * * *